US012616436B2

(12) United States Patent
Fukumoto et al.

(10) Patent No.: US 12,616,436 B2
(45) Date of Patent: May 5, 2026

(54) PULMONARY EMBOLISM DIAGNOSIS SUPPORT APPARATUS, PULMONARY EMBOLISM DIAGNOSIS SUPPORT METHOD, AND STORAGE MEDIUM

(71) Applicant: Konica Minolta, Inc., Tokyo (JP)

(72) Inventors: Takenori Fukumoto, Kamakura (JP); Noritsugu Matsutani, Kokubunji (JP); Yuzo Yamasaki, Fukuoka (JP); Kohtaro Abe, Fukuoka (JP); Kazuya Hosokawa, Fukuoka (JP); Takeshi Kamitani, Fukuoka (JP); Tomoyuki Hida, Fukuoka (JP); Kousei Ishigami, Fukuoka (JP)

(73) Assignee: KONICA MINOLTA, INC., Tokyo (JP)

( * ) Notice: Subject to any disclaimer, the term of this patent is extended or adjusted under 35 U.S.C. 154(b) by 359 days.

(21) Appl. No.: 18/169,375

(22) Filed: Feb. 15, 2023

(65) Prior Publication Data

US 2023/0263495 A1 Aug. 24, 2023

(30) Foreign Application Priority Data

| | | |
|---|---|---|
| Feb. 18, 2022 | (JP) | 2022-023408 |
| May 12, 2022 | (JP) | 2022-078594 |

(51) Int. Cl.
*A61B 6/00* (2024.01)
*A61B 6/50* (2024.01)

(52) U.S. Cl.
CPC ............ *A61B 6/5217* (2013.01); *A61B 6/504* (2013.01); *A61B 6/507* (2013.01)

(58) Field of Classification Search
CPC ....... A61B 6/5217; A61B 6/504; A61B 6/507; A61B 6/5211; A61B 6/50; G16H 30/40; G16H 50/50; G16H 50/20
See application file for complete search history.

(56) References Cited

U.S. PATENT DOCUMENTS

| | | | |
|---|---|---|---|
| 2007/0078357 A1* | 4/2007 | Kline | A61B 5/417 600/532 |
| 2009/0097731 A1* | 4/2009 | Sanada | A61B 6/469 382/132 |

(Continued)

FOREIGN PATENT DOCUMENTS

| | | |
|---|---|---|
| JP | 2004-523514 A | 8/2004 |
| JP | 2020-054580 A | 4/2020 |

(Continued)

OTHER PUBLICATIONS

Office Action, dated Dec. 9, 2025, which was issued for the corresponding Japanese Patent Application No. 2022-078594, 8 pages, with English translation.

*Primary Examiner* — Iriana Cruz

(74) *Attorney, Agent, or Firm* — LUCAS & MERCANTI, LLP

(57) ABSTRACT

A pulmonary embolism diagnosis support apparatus includes a hardware processor that: obtains a dynamic image of a chest of an examinee captured through radiographic dynamic imaging; analyzes blood flow in the dynamic image to generate blood flow information; generates background lungs information regarding background lungs of the examinee; automatically generates diagnosis support information regarding pulmonary embolism, based on the blood flow information and the background lungs information; and outputs the diagnosis support information regarding pulmonary embolism.

14 Claims, 9 Drawing Sheets

(56)　　　　　References Cited

U.S. PATENT DOCUMENTS

| | | | |
|---|---|---|---|
| 2013/0215388 A1* | 8/2013 | Imamura | G06T 7/254 |
| | | | 382/134 |
| 2020/0034964 A1* | 1/2020 | Shimamura | G06T 7/20 |
| 2023/0230241 A1* | 7/2023 | Lure | G16H 50/00 |
| | | | 382/128 |
| 2025/0061576 A1* | 2/2025 | Abe | G06T 7/0016 |

FOREIGN PATENT DOCUMENTS

| | | |
|---|---|---|
| WO | 2002/055544 A2 | 7/2002 |
| WO | 2014/091977 A1 | 6/2014 |

* cited by examiner

Figure 1:
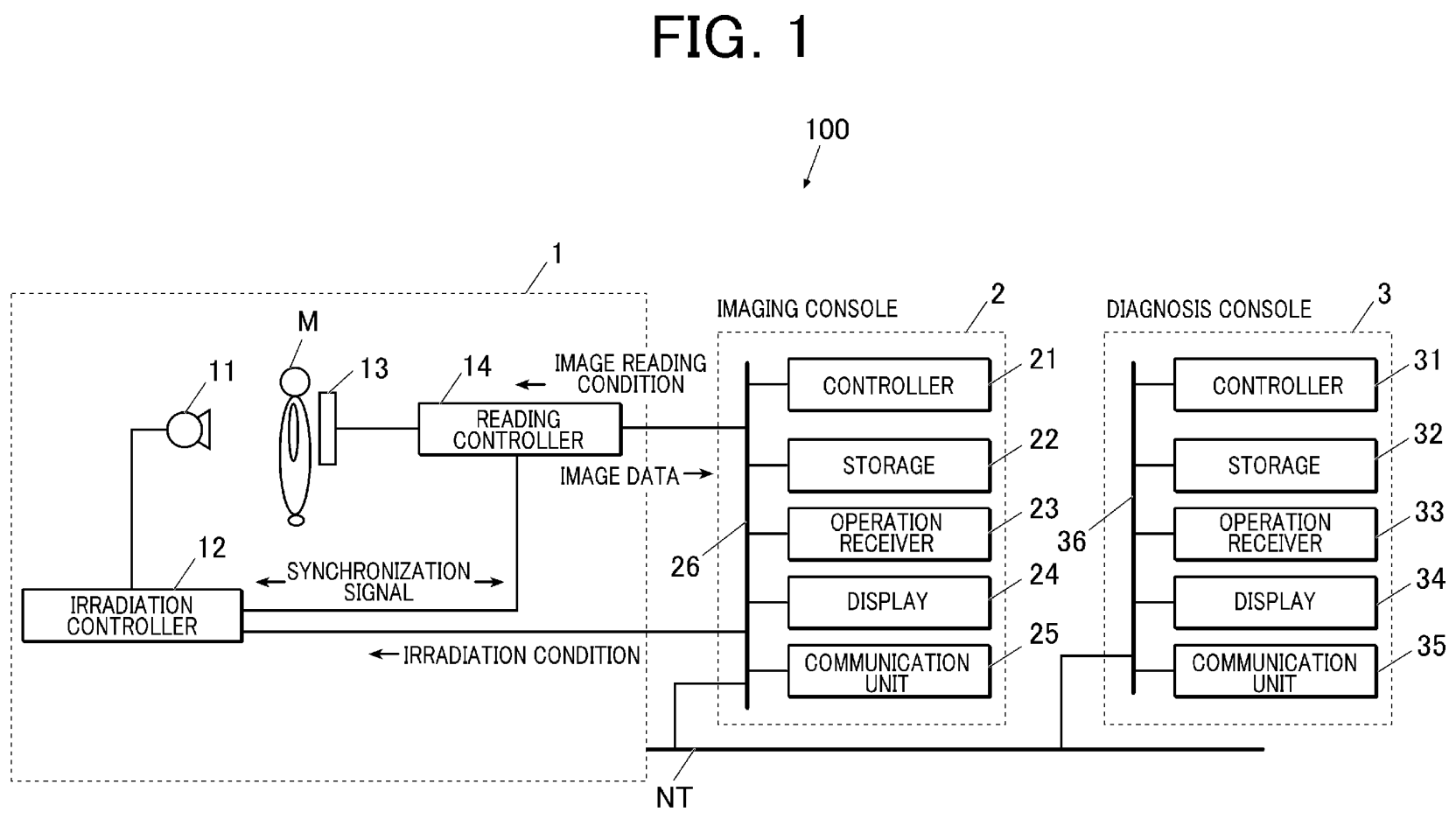

DIAGNOSIS CONSOLE 3

- CONTROLLER 31
- STORAGE 32
- OPERATION RECEIVER 33
- DISPLAY 34
- COMMUNICATION UNIT 35

36

IMAGING CONSOLE 2

- CONTROLLER 21
- STORAGE 22
- OPERATION RECEIVER 23
- DISPLAY 24
- COMMUNICATION UNIT 25

26

NT

1

IMAGE READING CONDITION

IMAGE DATA →

READING CONTROLLER 14

13

M

SYNCHRONIZATION SIGNAL →

← IRRADIATION CONDITION

11

12

IRRADIATION CONTROLLER

FIG. 2

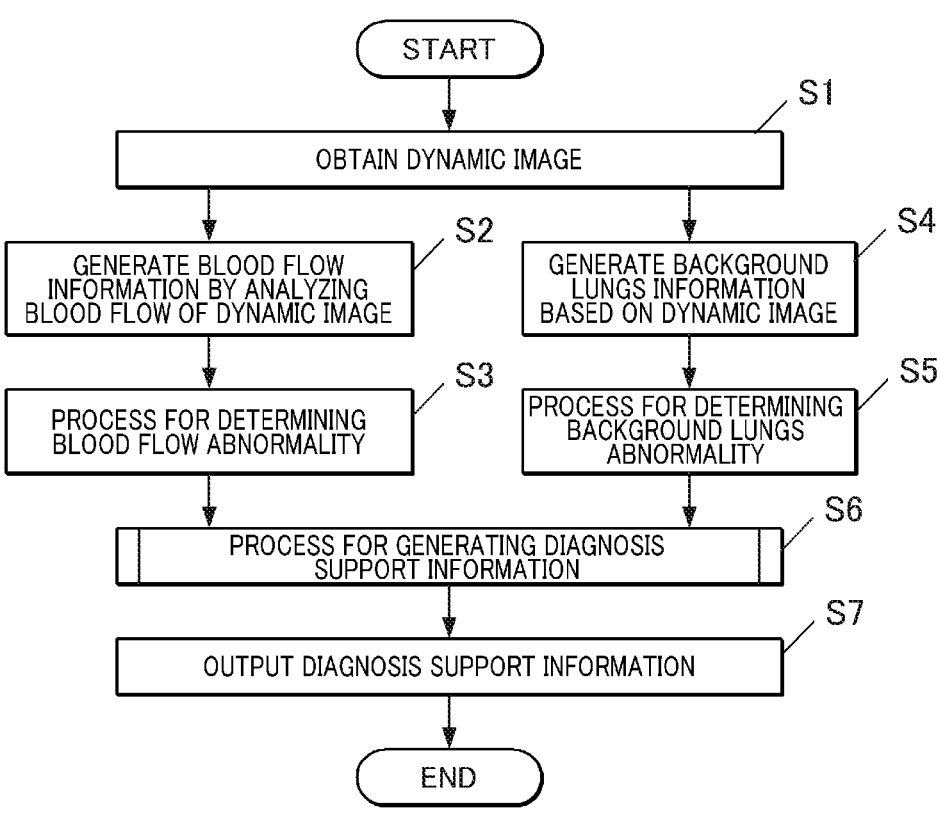

START

OBTAIN DYNAMIC IMAGE — S1

GENERATE BLOOD FLOW
INFORMATION BY ANALYZING
BLOOD FLOW OF DYNAMIC IMAGE — S2

GENERATE BACKGROUND
LUNGS INFORMATION
BASED ON DYNAMIC IMAGE — S4

PROCESS FOR DETERMINING
BLOOD FLOW ABNORMALITY — S3

PROCESS FOR DETERMINING
BACKGROUND LUNGS
ABNORMALITY — S5

PROCESS FOR GENERATING DIAGNOSIS
SUPPORT INFORMATION — S6

OUTPUT DIAGNOSIS SUPPORT INFORMATION — S7

END

FIG. 3

PULMONARY EMBOLISM DIAGNOSIS SUPPORT APPARATUS, PULMONARY EMBOLISM DIAGNOSIS SUPPORT METHOD, AND STORAGE MEDIUM

CROSS-REFERENCE TO RELATED APPLICATIONS

The entire disclosure of Japanese Patent Applications No. 2022-023408 filed on Feb. 18, 2022 and No. 2022-078594 filed on May 12, 2022 is incorporated herein by reference in its entirety.

TECHNICAL FIELD

The present disclosure relates to a pulmonary embolism diagnosis support apparatus, a pulmonary embolism diagnosis support method, and a storage medium.

DESCRIPTION OF THE RELATED ART

Diagnosis of pulmonary embolism involves checking presence of an embolus (e.g., a thrombus) and decrease in pulmonary blood flow caused by the embolus. Known methods and modalities used for diagnosing pulmonary embolism include pulmonary arteriography, contrast-enhanced computed tomography (CT), and scintigraphy of pulmonary ventilation and blood flow. Among these, contrast-enhanced CT has become a standard method. However, contrast-enhanced CT may cause contrast media allergy and radiation exposure (in particular, for expectant mothers and infants). Scintigraphy of pulmonary ventilation and blood flow does not cause contrast media allergy but requires administration of radiopharmaceuticals, by which a patient may be exposed to radiation.

As a criterion for diagnosing pulmonary embolism in scintigraphy, a patient is diagnosed with pulmonary embolism if the result of pulmonary ventilation scintigraphy shows no abnormalities but the result of pulmonary blood flow scintigraphy shows a segmental defect, for example. A patient is also diagnosed with pulmonary embolism if the background lungs show no abnormalities in plain X-ray images or in chest CT but the result of pulmonary blood flow scintigraphy shows a segmental defect.

JP2020-54580A discloses an apparatus that identifies a thrombus region based on medical images obtained by plain CT. In order to deal with a difficulty of obtaining a large amount of data showing correct regions of a disease, the apparatus learns, as training data, thrombus regions/infarct regions identified in brain CT images of patients (examinees) having a cerebral thrombosis/cerebral infarction. Thus, the apparatus enhances accuracy of identifying a thrombus.

Dynamic state diagnosis has attracted attention as a new diagnosis method. Dynamic state diagnosis is advantageous in that (i) it requires lower radiation exposure than CT, (ii) it is as quick as plain X-ray imaging, and (iii) it provides more information than plain X-ray imaging. For example, WO2014091977A1 describes performing blood flow analysis based on a dynamic image.

SUMMARY OF THE INVENTION

However, researches of the dynamic state for diagnosing thrombi have not progressed sufficiently. WO2014091977A1 only indicates the applicability of dynamic imaging for diagnosing thrombi.

In order to increase accuracy in identifying thrombi in dynamic state diagnosis, artificial intelligence (AI) may be applied, as disclosed in JP2020-54580A. However, the blood flow analysis based on a dynamic image does not detect a thrombus itself but shows an abnormality of blood flow at peripheral regions rather than at the thrombi. Therefore, when the result of blood flow analysis indicates a poor blood flow region, it is difficult to identify the cause of the poor blood flow (whether the poor blood flow is caused by a thrombus or by any other disease, such as chronic obstructive pulmonary disease (COPD), pneumothorax, bulla (a disease that causes bloated bubbles of pulmonary alveoli), or interstitial pneumonia). In other words, blood flow analysis may show the same result even if causes (diseases) are different. Even if an AI learns a set of data having correct answers regarding thrombi based on the result of the dynamic state analysis, the AI cannot avoid the possibility of wrongly determining that a patient has a thrombus, based on the blood flow analysis result of the patient having a disease different from a thrombus. It is therefore difficult to increase accuracy in diagnosing a thrombus based only on the blood flow analysis of a dynamic image.

As described above, the known methods for diagnosing pulmonary embolism require administration of contrast media/radiopharmaceuticals to patients, which is a burden on the patients. The known methods also require labor-consuming and time-consuming preparation. Further, modalities used in the known methods are expensive. In terms of cost and invasiveness to a patient, such modalities may not be repetitively used for imaging for the purpose of diagnosis.

The present invention has been conceived in view of the above issues. Objects of the present invention include enabling diagnosis of pulmonary embolism that lessens burdens on patients, that is quick with a low cost, and that can be performed repetitively.

To achieve at least one of the above objects, according to an aspect of the present invention, a pulmonary embolism diagnosis support apparatus includes a hardware processor that: obtains a dynamic image of a chest of an examinee captured through radiographic dynamic imaging; analyzes blood flow in the dynamic image to generate blood flow information; generates background lungs information regarding background lungs of the examinee; automatically generates diagnosis support information regarding pulmonary embolism, based on the blood flow information and the background lungs information; and outputs the diagnosis support information regarding pulmonary embolism.

According to another aspect of the present invention, a pulmonary embolism diagnosis support method includes: obtaining a dynamic image of a chest of an examinee captured through radiographic dynamic imaging; analyzing blood flow in the dynamic image to generate blood flow information; generating background lungs information regarding background lungs of the examinee; automatically generating diagnosis support information regarding pulmonary embolism, based on the blood flow information and the background lungs information; and outputting the diagnosis support information regarding pulmonary embolism.

According to another aspect of the present invention, a nontransitory computer-readable storage medium stores a program that causes a compute to: obtain a dynamic image of a chest of an examinee captured through radiographic dynamic imaging; analyzing blood flow in the dynamic image to generate blood flow information; generate background lungs information regarding background lungs of the examinee; automatically generate diagnosis support information regarding pulmonary embolism, based on the blood flow information and the background lungs information; and output the diagnosis support information regarding pulmonary embolism.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 1 shows an overall configuration of an imaging system according to a first embodiment of the present invention;

FIG. 2 is a flowchart of a first pulmonary embolism diagnosis support process;

FIG. 3 is an example of a dynamic image showing a chest;

DETAILED DESCRIPTION

Figure 4:
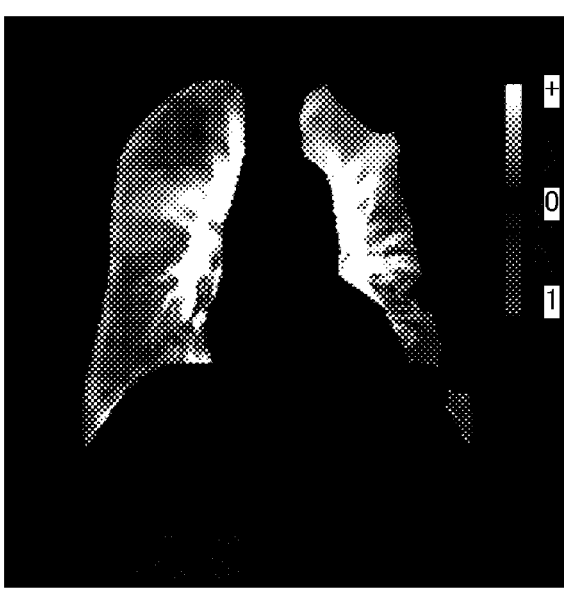
FIG. 4 is an example of a blood flow image.

Hereinafter, embodiments of the present invention will be described with reference to the drawings. However, the scope of the invention is not limited to the illustrated examples.

First Embodiment

[Configuration of Imaging System]

FIG. 1 shows an overall configuration of an imaging system 100 in a first embodiment.

As shown in FIG. 1, the imaging system 100 includes: an imaging device 1; an imaging console 2 connected to the imaging device 1 via a communication cable or the like; and a diagnostic console 3 connected to the imaging console 2 via a communication network NT, such as a LAN (local area network). These components constituting the imaging system 100 conform to DICOM (Digital Image and Communications in Medicine) standard and communicate with one another in accordance with the DICOM standard

[Configuration of Imaging Device]

The imaging device 1 is configured to image the dynamic state, such as the change in the shape of lungs that expand and contract by respiration and pulsation of the heart. In dynamic imaging, a plurality of images showing the dynamic state of a subject M is obtained by repeatedly emitting pulsed radiation, such as X-rays, to the subject M at predetermined time intervals (pulse emission) or by continuously emitting radiation without a break to the subject M at a low dose rate (continuous emission). A series of images obtained by dynamic imaging is called a dynamic image. Images constituting a dynamic image are called frame images. Dynamic imaging can obtain functional information (physical information) of the subject M as well as morphological information of the subject M. The imaging device 1 can also obtain still images. Herein, the subject M is the chest of an examinee.

A radiation source 11 is positioned to face a radiation detector 13 with the subject M inbetween. The radiation source 11 emits radiation (X-rays) to the subject M under the control of an irradiation controller 12.

The irradiation controller 12 is connected to the imaging console 2. The irradiation controller 12 controls the radiation source 11 to perform radiography, based on irradiation conditions input by the imaging console 2. The irradiation conditions input by the imaging console 2 include the pulse rate, the pulse width, the pulse interval, the number of frames to be captured per one time of imaging, current values of an X-ray tube, voltage values of the X-ray tube, and a type of added filter, for example. The pulse rate is the number of times of radiation emissions per second. The pulse rate corresponds to the frame rate, which is described below. The pulse width is a duration of one radiation emission. The pulse interval is an interval between the start of one radiation emission and the start of the next radiation emission. The pulse interval corresponds to the frame interval, which is described below.

The radiation detector 13 is a semiconductor image sensor, such as a flat panel detector (FPD). The FPD includes a substrate, such as a glass substrate, on which detection elements (pixels) are arranged at predetermined positions in a matrix. The detection elements detect radiation depending on the intensity of radiation that has been emitted from the radiation source 11 and that has passed through at least the subject M, convert the detected radiation into electric signals, and accumulate the electric signals. Each of the pixels has a switch, such as a thin film transistor (TFT). Types of the FPD include an indirect conversion type that converts X-rays into electric signals by using photoelectric conversion elements via a scintillator and a direct conversion type that directly converts X-rays into electric signals. Either type can be used.

A reading controller 14 is connected to the imaging console 2. The reading controller 14 controls the switches of the pixels of the radiation detector 13 and switches the pixels to read the electric signals accumulated in the pixels, based on image reading conditions input by the imaging console 2. The reading controller 14 thus obtains image data. The image data is a frame image constituting a dynamic image or a still image. When a structure is present between the radiation source 11 and the radiation detector 13, the amount of radiation that reaches the radiation detector 13 decreases due to the structure. Therefore, pixel values (density values) of pixels constituting the image data vary depending on the structure of the subject M. The reading controller 14 outputs the obtained dynamic image or still image to the imaging console 2. The image reading conditions include the frame rate, the frame interval, the pixel size, and the image size (matrix size), for example. The frame rate is the number of frame images obtained per second. The frame rate corresponds to the pulse rate. The frame interval is a time interval between the start of one frame image obtaining action to the start of the next frame image obtaining action. The frame interval corresponds to the pulse interval.

The irradiation controller 12 and the reading controller 14 are connected to each other so that they can exchange synchronization signals to synchronize the irradiation operation and the image reading operation.

[Configuration of Imaging Console]

The imaging console 2 outputs the irradiation conditions and the image reading conditions to the imaging device 1 and controls radiographic imaging operation and radiographic-image reading operation of the imaging device 1.

As shown in FIG. 1, the imaging console 2 includes a controller 21, a storage 22, an operation receiver 23, a display 24, and a communication unit 25. These components are connected via a bus 26.

The controller 21 includes a central processing unit (CPU) and a random access memory (RAM). The CPU of the controller 21 reads a system program and various process programs stored in the storage 22 in accordance with the manipulation of the operation receiver 23, loads the read programs in the RAM, and performs various processes in accordance with the loaded programs. The CPU of the controller 21 thus centrally controls operations of the components constituting the imaging console 2 and the irradiation operation and the reading operation of the imaging device 1.

The storage 22 is constituted of a nonvolatile semiconductor memory and/or a hard disk, for example. The storage 22 stores various kinds of data, such as programs to be executed by the controller 21, parameters for performing processes of the programs, and process results. For example, the storage 22 stores the irradiation conditions and the image reading conditions in association with sites of subjects. The programs are stored in the form of computer-readable program codes. The controller 21 successively performs operations in accordance with the program codes.

The operation receiver 23 includes a keyboard including cursor keys, number input keys and various function keys, and a pointing device, such as a mouse. The operation receiver 23 outputs, to the controller 21, a command signal input by a key operation on the keyboard or by a mouse operation. The operation receiver 23 may include a touchscreen on the display screen of the display 24. In this case, the operation receiver 23 outputs command signals input on the touchscreen to the controller 21.

The display 24 is constituted of a monitor, such as a liquid crystal Display (LCD), and displays instructions input via the operation receiver 23 and data in accordance with commands of display signals input by the controller 21.

The communication unit 25 includes a LAN adapter, a modem, and/or a terminal adapter (TA). The communication unit 25 controls data transmission and reception to and from devices connected to the communication network NT.

[Configuration of Diagnosis Console]

The diagnosis console 3 obtains dynamic images, still images, and so forth from the imaging console 2 and displays the obtained images and/or the result of analyzing the images, thereby supporting diagnosis by doctors. In particular, the diagnosis console 3 is used as a pulmonary embolism diagnosis support apparatus that generates diagnosis support information regarding pulmonary embolism, based on a dynamic image and so forth. The diagnosis console 3 is a computer, such as a personal computer or a workstation.

Pulmonary embolism is basically pulmonary thromboembolism (PTE). Types of PTE are classified into acute PTE and chronic PTE.

Acute PIE is so-called PTE.

Chronic PTE is a case where a thrombus (thrombi) in a pulmonary artery becomes organized and chronic. Chronic PTE complicated with pulmonary hypertension is called chronic thromboembolic pulmonary hypertension (CTEPH).

As shown in FIG. 1, the diagnosis console 3 includes a controller 31 (hardware processor), a storage 32, an operation receiver 33, a display 34, and a communication unit 35. These components are connected via a bus 36.

The controller 31 includes a CPU and a RAM. The CPU of the controller 31 reads a system program and various process programs stored in the storage 32 in accordance with the manipulation of the operation receiver 33, loads the read programs in the RAM, and performs various processes in accordance with the loaded programs. The CPU of the controller 31 thus centrally controls operations of the components constituting the diagnosis console 3.

The storage 32 is constituted of a nonvolatile semiconductor memory and/or a hard disk, for example. The storage 32 stores various kinds of data, such as programs to be executed by the controller 31, parameters for performing processes in accordance with the programs, and process results. The programs are stored in the form of computer-readable program codes. The controller 31 successively performs operations in accordance with the program codes.

The operation receiver 33 includes a keyboard including cursor keys, number input keys and various function keys, and a pointing device, such as a mouse. The operation receiver 33 outputs, to the controller 31, a command signal input by a key operation on the keyboard or by a mouse operation. The operation receiver 33 may include a touchscreen on the display screen of the display 34. In this case, the operation receiver 33 outputs command signals input via the touchscreen to the controller 31.

The display 34 is constituted of a monitor, such as an LCD, and displays various contents in accordance with commands of display signals input by the controller 31.

The communication unit 35 includes a LAN adapter, a modem, and/or a TA, and controls data transmission and reception to and from devices connected to the communication network NT.

Via the communication unit 35, the controller 31 obtains a dynamic image, which is obtained through radiographic dynamic imaging of the chest of the examinee. The controller 31 thus functions as an obtaining unit.

The controller 31 analyzes the blood flow based on the dynamic image to generate blood flow information. The controller 31 thus functions as a first generating unit.

The controller 31 automatically determines whether there is an abnormality in the blood flow, based on the blood flow information. The controller 31 thus functions as a first determining unit. The controller 31 also identifies the position/region of the abnormal blood flow.

The controller 31 generates background lungs information regarding the background lungs of the examinee who is the subject of dynamic imaging. The controller 31 thus functions as a second generating unit. The background lungs refer to the lungs themselves. In the first embodiment, the controller 31 generates the background lungs information, based on one or more frame images in the dynamic image.

The controller 31 automatically determines whether there is an abnormality in the background lungs, based on the background lungs information. The controller 31 thus functions as a second determining unit. If the examinee is suffering from COPD or interstitial pneumonia for example, his/her lungs themselves are not in the normal state. The controller 31 also identifies the position/region of the abnormal part of the background lungs.

The controller 31 generates diagnosis support information regarding pulmonary embolism, based on the blood flow information and the background lungs information. The controller 31 thus functions as a third generating unit. More specifically, the controller 31 generates diagnosis support information regarding pulmonary embolism, based on (i) the result of determination on whether the blood flow is abnormal and (ii) the result of determination on whether the background lungs are abnormal.

For example, when the blood flow is abnormal but the background lungs are normal, the controller 31 generates diagnosis support information that indicates the possibility of pulmonary embolism.

When the blood flow is abnormal and part of the background lungs corresponding to the abnormal blood flow region are also abnormal, the controller 31 generates diagnosis support information that indicates the possibility of a disease different from pulmonary embolism.

When the blood flow is normal, the controller 31 generates diagnosis support information that indicates no possibility of pulmonary embolism.

The controller 31 outputs diagnosis support information regarding pulmonary embolism. The controller 31 thus functions as an outputting unit. For example, the controller 31 displays diagnosis support information regarding pulmonary embolism on the display 34.

[Operation of Imaging System]

Next, the operation of the imaging system 100 is described.

[Operation of Imaging Device and Imaging Console]

First, imaging operation performed by the imaging device 1 and the imaging console 2 is described. The controller 21 of the imaging console 2 sets irradiation conditions to the irradiation controller 12 and sets image reading conditions to the reading controller 14.

The controller 21 outputs an instruction to start obtaining a dynamic image to the irradiation controller 12 and the reading controller 14 and controls dynamic imaging More specifically, the radiation source 11 emits radiation at a pulse interval that is set to the irradiation controller 12, and the reading controller 14 obtains image data (frame images) from the radiation detector 13 and outputs the image data to the imaging console 2. When a predetermined number of frame images is obtained, the controller 21 stops the imaging operation by outputting an instruction to end imaging to the irradiation controller 12 and the reading controller 14. The controller 21 stores the obtained frame images in association with their ordinal numbers in the imaging order (frame numbers) in the storage 22.

The controller 21 displays the dynamic image on the display 24. When a person who performs imaging confirms that the dynamic image is appropriate for diagnosis and inputs an confirmation instruction via the operation receiver 23, the controller 21 attaches patient information (e.g., patient ID and patient name of the examinee) and examination information to each of the frame images obtained in the dynamic imaging and sends the frame images to the diagnosis console 3 via the communication unit 25.

8

[Operation of Diagnosis Console]

Next, operation of the diagnosis console 3 is described.

FIG. 2 is a flowchart showing the first pulmonary embolism diagnosis support process that is performed by the diagnosis console 3. The process is performed before or while a doctor makes diagnosis based on a dynamic image. The process is performed by the controller 31 in accordance with the program stored in the storage 32.

When the imaging device 1 performs radiographic dynamic imaging of the chest of the examinee, the controller 31 obtains the dynamic image generated by the imaging device 1 from the imaging console 2 via the communication unit 35 (Step S1). The dynamic image consists of multiple frame images. The controller 31 stores the obtained dynamic image in the storage 32.

FIG. 3 shows an example of the dynamic image of the chest.

The controller 31 performs blood flow analysis based on the dynamic image and generates blood flow information (Step S2). More specifically, the controller 31 generates an image(s) and values indicating the blood flow, based on signal values of pixels constituting the regions related to pulmonary blood flow in the dynamic image.

Signal values in the chest dynamic image change according to the change of the blood flow volume in the pulmonary artery, which is caused by the blood flow ejected by the heart. More specifically, when the blood flow volume in the pulmonary artery increases at the systolic phase, the signal values in the dynamic image increase. On the other hand, when the blood flow volume in the pulmonary artery decreases at the diastolic phase, the signal values in the dynamic image decrease. In the blood flow analysis based on the chest dynamic image, the image is subjected to post-processing (e.g., the image is colored) based on changes in signal values from the end diastole. Thus, changes in the blood flow volume in the pulmonary artery are visualized and quantified.

Following are specific examples of the blood flow information.

(A1) Change Amount of Signal Values from Reference Frame

The controller 31 calculates the change amount of signal values of the ROI (a predetermined region in the lung field) from a reference frame, based on frame images constituting the chest dynamic image. The reference image is a frame corresponding to the end diastole, for example. In order to extract the signal change associated with pulsations, a filter that passes only the frequency range around the cardiac cycle is used.

(A2) Blood Flow Image

The controller 31 colors each of the frames, based on the change amount obtained in the above (A1) and a predetermined coloring table (table in which change amounts are associated with colors) to generate a series of frame images (blood flow image). The series of frame images shows the change in blood flow.

FIG. 4 is an example of the blood flow image. The blood flow image indicates the change amount of signal values and the region of poor blood flow by different colors. Frames constituting the blood flow image are displayed along the passage of time so that the user can easily recognize the change in blood flow.

(A3) Representative Image

The controller 31 generates a representative image (still image), based on the series of frame images that are colored in the above (A2). Examples of the representative image include: an image processed with maximum intensity projection (MIP); an image processed with minimum intensity projection (MinIP); and a specific single frame image.

The MIP is a process to obtain the maximum signal value (herein, the color corresponding to the maximum change amount) for each of the pixels (positions) along the time variation and adopt the maximum signal value as the pixel value.

The MinIP is a process to obtain the minimum signal value (herein, the color corresponding to the minimum change amount) for each of the pixels (positions) along the time variation and adopt the minimum signal value as the pixel value.

(A4) Blood Flow Decrease Region

The controller 31 colors a region or draws a boundary of the region that has the change amount equal to or less than a predetermined threshold with respect to the representative image, which is generated in the above (A3). The controller 31 thus displays the region to be distinguishable from the other regions.

Figure 5:
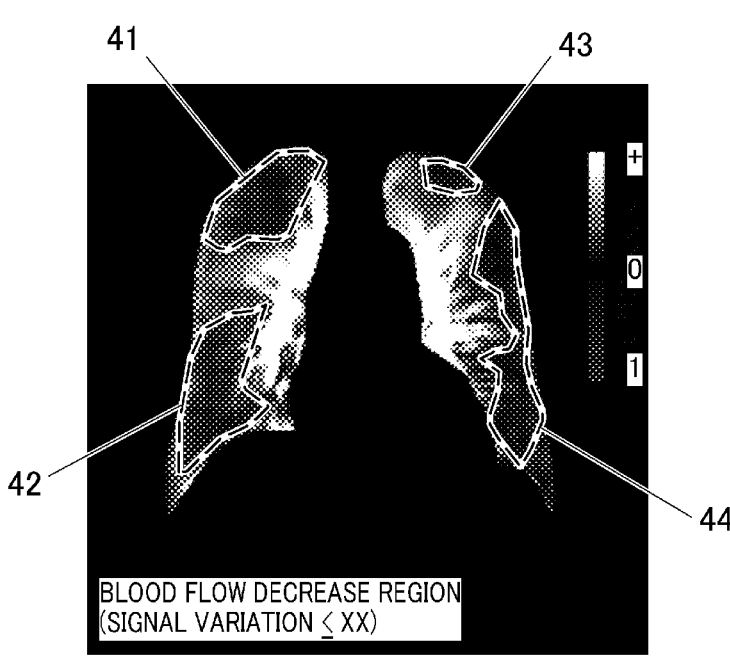
FIG. 5 is a representative image on which blood flow decrease regions are shown.

FIG. 5 is the representative image (still image) indicating regions 41 to 44 that are bordered with clash lines. Each of the regions 41 to 44 has a change amount in signal values equal to or less than a threshold and has a decreased blood flow.

Herein, the area of the region having the change amount equal to or less than a predetermined threshold may be calculated, and the area may be used as the blood flow information.

(A5) Graph of Time Variation

The controller 31 graphically shows the time variation in the signal value or the change amount obtained in the above (A1).

Figure 6:
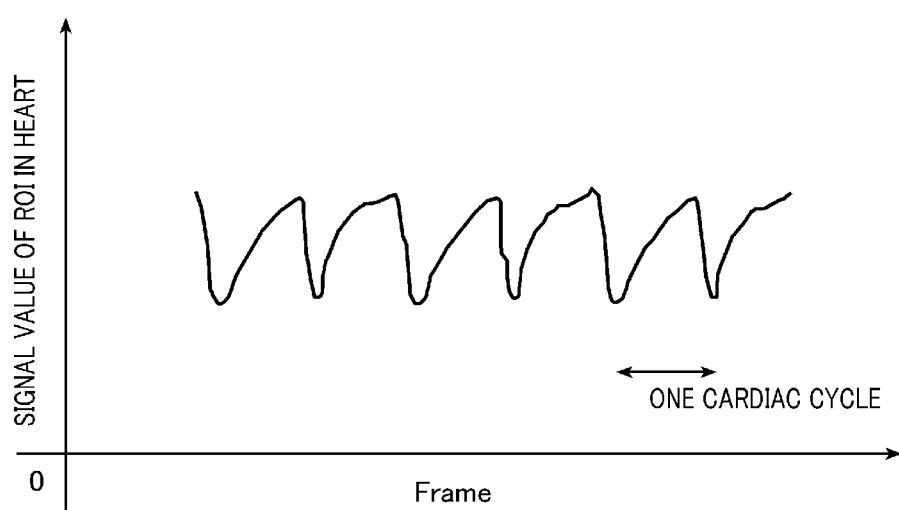
FIG. 6 is a graph showing time variation of signal values in a region of interest (ROI) in the heart.

FIG. 6 is a graph showing the time variation in the signal value of the ROI in the heart.

Figure 7:
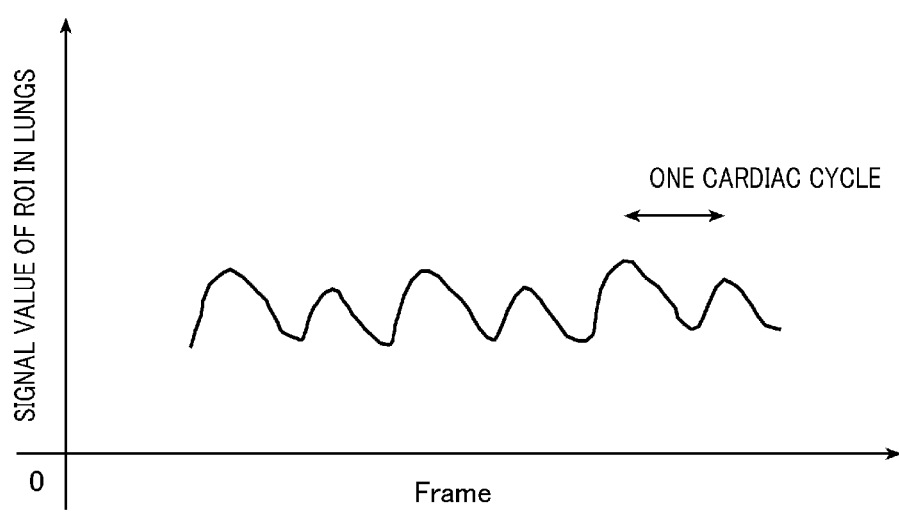
FIG. 7 is a graph showing time variation of signal values in a region of interest (ROI) in the lungs.

FIG. 7 is a graph showing the time variation in the signal value of the ROI in the lungs.

Next, the controller 31 performs a process for determining blood flow abnormality (Step S3). More specifically, the controller 31 automatically determines whether the blood flow is abnormal, based on the blood flow information. The controller 31 determines the region in which the blood flow decreases as being abnormal. For example, when the controller 31 detects multiple segmental defects or a greater wedge-shaped defect image (accumulation decrease region) in the series of frame images obtained by the blood analysis, the controller 31 determines that the blood flow is abnormal. The controller 31 also determines whether the blood flow is abnormal, based on the comparison of values/graphs of the blood flow with a predetermined threshold or a reference range.

The controller 31 also identifies a region of the abnormal blood flow (abnormal blood flow region). For example, the lung field is divided into six regions (right and left, top, middle and bottom), and the controller 31 identifies a region having the abnormal blood flow among the six regions. The controller 31 stores the abnormal blood flow region in the storage 32.

Figure 8A:
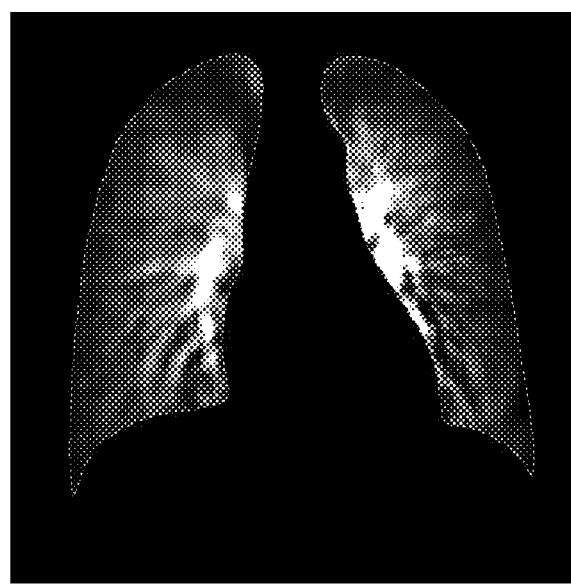
FIG. 8A is an example of a normal blood flow image obtained by dynamic state analysis.
Figure 8B:
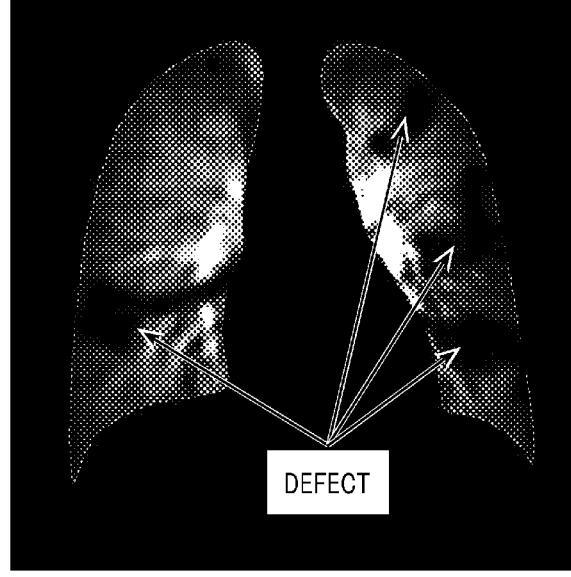
FIG. 8B is an example of a blood flow image of chronic thromboembolic pulmonary hypertension (CTEPH) obtained by dynamic state analysis.

FIG. 8A shows an example of a normal blood flow image obtained by dynamic state analysis (the series of frame images that are colored based on the change amount in the signal value). FIG. 8B is an example of a blood flow image of CTEPH obtained by dynamic state analysis. The blood flow image of a CTEPH patient shows more segmental defects or a greater wedge-shaped defect image, as compared with the example of the normal blood flow image.

After Step S1, the controller 31 also generates background lungs information, based on one or more frame images constituting the dynamic image (Step S4).

Following is a specific example of the background lungs information.

(B1) High-Definition Image

The controller 31 generates a high-definition image (still image) based on multiple frame images constituting a dynamic image. Although a dynamic image has a relatively low resolution, a high-definition image can be generated from multiple frame images constituting the dynamic image by applying a super-resolution technique, for example.

Figure 9:
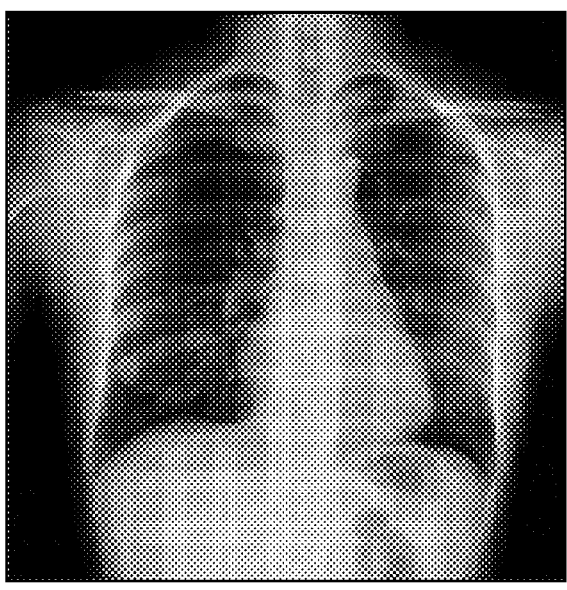
FIG. 9 is an example of a high-definition image generated as background lungs information.

FIG. 9 is an example of a high-definition image generated as the background lungs information.

(B2) Dynamic Image Itself

The controller 31 uses a dynamic image itself (multiple frame images) as the background lungs information. All the frame images constituting the dynamic image may be used as the background lungs information, or part of all the frame images may be used as the background lungs information.

(B3) Processed Dynamic Image

The controller 31 uses a processed dynamic image (e.g., enhancement process in the spatial direction or in the time direction, smoothing) as the background lungs information.

Figure 10:
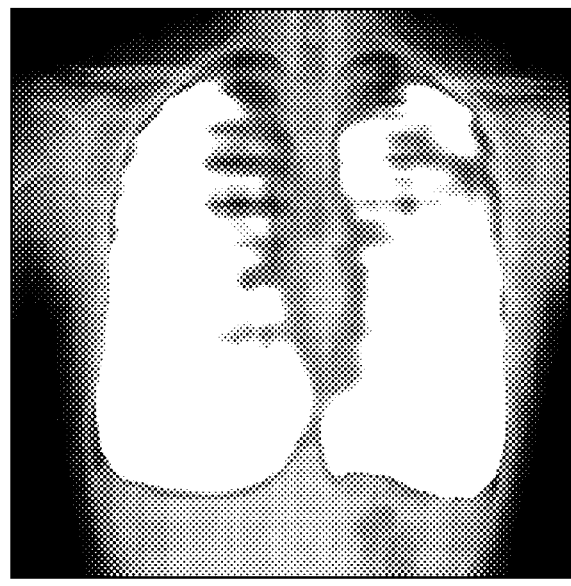
FIG. 10 is an example of an image obtained by extracting signal value changes caused by respiration from a dynamic image.

FIG. 10 shows an image obtained by extracting changes in signal values caused by respiration from a dynamic image. The image shows changes in signal values that synchronize with respiration in the chest dynamic image. In FIG. 10, in each of pixels (positions) constituting each of the frame images, when the change in the signal value along with inhalation and exhalation of respiration is equal to or greater than a predetermined threshold, the pixel is colored (white in FIG. 10).

Figure 11:
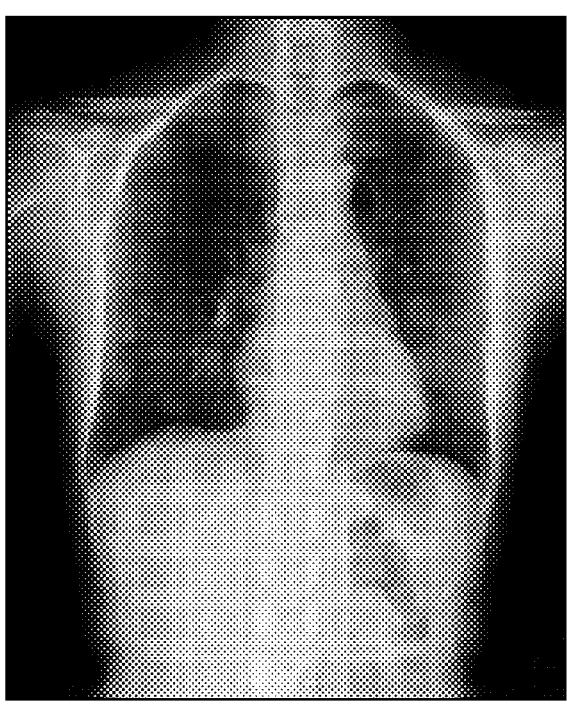
FIG. 11 is an example of a dynamic image on which bone suppression processing has been performed.

FIG. 11 shows an example of a dynamic image on which bone suppression processing has been performed. By performing bone suppression processing on the dynamic image, the organizations that overlap with bones become more recognizable and discriminative.

Figure 12:
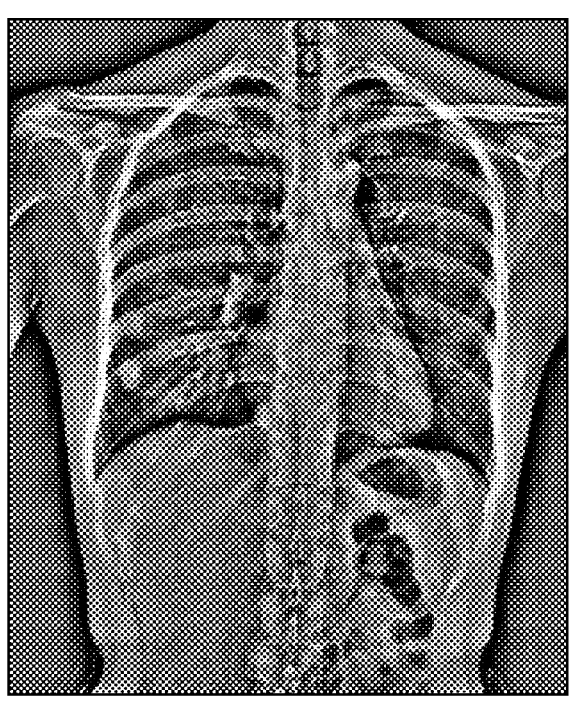
FIG. 12 is an example of a dynamic image on which frequency enhancement processing has been performed.

FIG. 12 shows an example of a dynamic image on which frequency enhancement processing has been performed. By performing frequency enhancement processing on the dynamic image, the contours of bones and organs become conspicuous and more discriminative (B4) Single Frame Image.

The controller 31 uses a certain single frame image in the dynamic image as the background lungs information. For example, among the frame images constituting the dynamic image, the controller 31 determines a frame image that shows the maximum change caused by biological movements as the background lungs information.

(B5) Processed Single Frame Image

The controller 31 uses a certain single frame image in the dynamic image and that has been processed (e.g., enhancement process, smoothing) as the background lungs information.

(B6) Graph Showing Change Amount of Specific Component

The controller 31 performs processing of tracking a specific component (e.g., diaphragm, width of the thorax, diameter of the respiratory tract, area of the lung field) in the frames of the dynamic image and graphically shows the change amount of the specific component.

Figure 13:
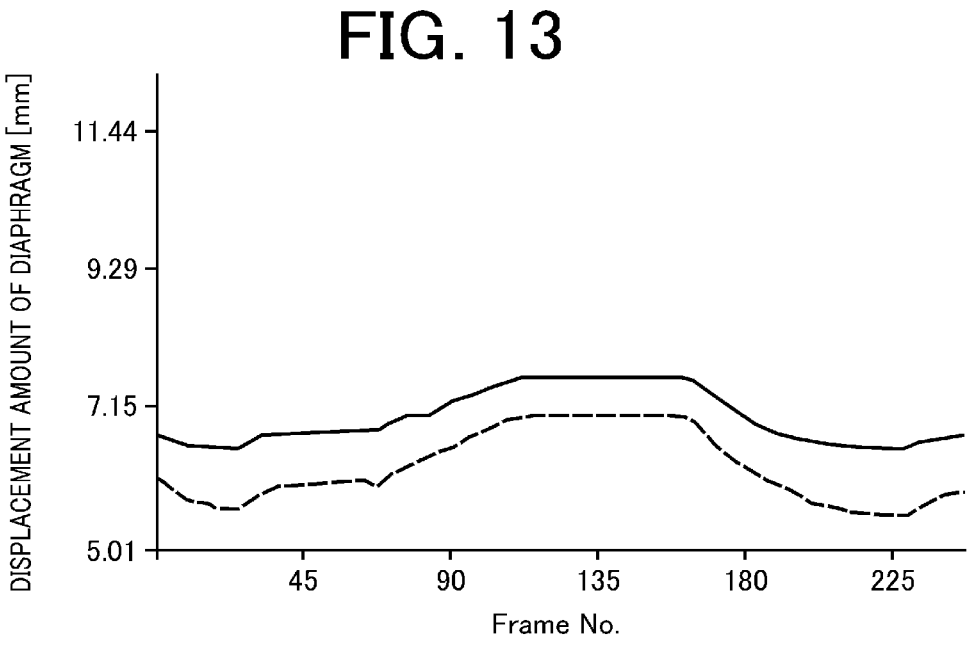
FIG. 13 is an example of a graph showing time variation of displacement amounts of the diaphragm.

FIG. 13 shows time variation of the displacement amount of the diaphragm. The movement of the lungs is quantified by the displacement amount of the diaphragm, for example, so that the function of the background lungs can be judged objectively.

Next, the controller 31 performs a process for determining background lungs abnormality (Step S5). More specifically, the controller 31 automatically determines whether there is an abnormality in the background lungs, based on the background lungs information. For example, the controller 31 analyzes the background lungs information (e.g., a high-definition image, an image on which bone suppression processing has been performed). When morphological abnormalities are found (e.g., a shadow is detected in the background lung), the controller 31 determines that the background lungs are abnormal. The controller 31 also determines whether the background lungs are abnormal, based on the comparison of values/graphs showing the state of the background lungs with a predetermined threshold or a reference range.

The controller 31 also identifies an abnormal region in the background lungs (abnormal background lungs region). For example, the lung field is divided into six regions (right and left, top, middle and bottom), and the controller 31 identifies a region in which the background lungs are abnormal among the six regions. The controller 31 stores the abnormal background lungs region in the storage 32.

After Step S3 and Step S5, the controller 31 performs a process for generating diagnosis support information (Step S6). In the process for generating diagnosis support information, the diagnosis support information on pulmonary embolism is automatically generated, based on (i) the result of determination on whether the blood flow is abnormal (including abnormal blood flow region), based on the blood flow information and (ii) the result of determination on whether the background lungs are abnormal (including abnormal background lungs region), based on the background lungs information.

Figure 14:
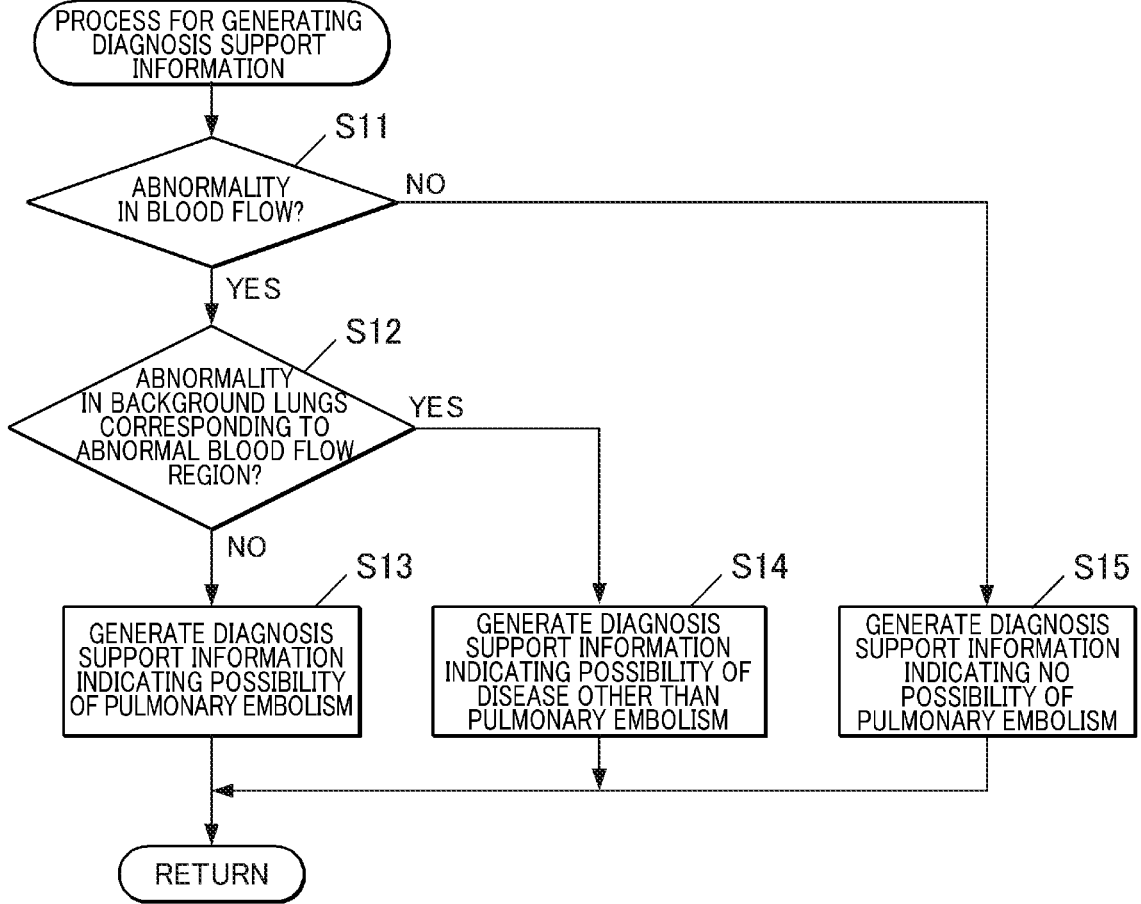
FIG. 14 is a flowchart of a process for generating diagnosis support information.

The process for generating diagnosis support information is described in detail with reference to FIG. 14.

When the blood flow is abnormal (Step S11: YES) but the background lungs corresponding to the abnormal blood flow region are normal (Step S12: NO), the controller 31 generates diagnosis support information that indicates the possibility of pulmonary embolism (Step S13). That is, when the blood flow is abnormal but the background lungs (entire lung region) are normal, the controller 31 generates diagnosis support information that indicates the possibility of pulmonary embolism. Further, when (i) the blood flow is abnormal, (ii) the background lungs are also abnormal, and (iii) the abnormal blood flow region does not correspond to the abnormal background lungs region, the controller 31 generates diagnosis support information that indicates the possibility of pulmonary embolism.

When the blood flow is abnormal (Step S11: YES) and the background lungs corresponding to the abnormal blood flow region are abnormal (Step S12: YES), namely when the abnormal blood flow region corresponds to the abnormal background lungs region, the controller 31 generates diagnosis support information that indicates the possibility of a disease different from pulmonary embolism (Step S14).

When the blood flow is normal (Step S11: NO), the controller 31 generates diagnosis support information that indicates no possibility of pulmonary embolism (Step S15).

After Step S13, S14 or S15, the process returns to FIG. 2. The controller 31 outputs the diagnosis support information regarding pulmonary embolism (Step S7). More specifically, the controller 31 displays diagnosis support information regarding pulmonary embolism on the display 34. The user views the diagnosis support information and recognizes the possibility of pulmonary embolism or the possibility of a disease different from pulmonary embolism of the patient (subject of diagnosis).

The first pulmonary embolism diagnosis support process ends.

As described above, in the first embodiment, the diagnosis support information regarding pulmonary embolism is generated based on the dynamic image. The first embodiment does not require administration of a contrast agent or radio-pharmaceutical to the patient, and is therefore low invasive. Further, the imaging device 1, which performs dynamic imaging, is less expensive and requires less preparation for examination than modalities that have been conventionally used for diagnosing pulmonary embolism. Thus, the first embodiment allows quick and low-cost diagnosis of pulmonary embolism that can be repeated and that reduces burdens on the patient.

Further, an abnormality in blood flow can be automatically identified based on the blood flow information without assistance of humans.

Further, an abnormality in the background lungs can be automatically identified based on the background lungs information without assistance of humans.

Further, when the background lungs are normal but the blood flow is abnormal, it is considered that an embolus (e.g., a thrombus) is present, and diagnosis support information that indicates the possibility of pulmonary embolism is generated.

When the blood flow is abnormal and the background lungs corresponding to the abnormal blood flow region are also abnormal, it is considered that the lungs themselves have a disease rather than that an embolus is present. Therefore, diagnosis support information that indicates the possibility of a disease different from pulmonary embolism is generated.

When the blood flow is normal, diagnosis support information that indicates no possibility of pulmonary embolism is generated.

Further, the background lungs information is generated based on one or more frame images constituting a dynamic image. Therefore, the patient does not have to undergo an examination other than dynamic imaging to generate the background lungs information. This reduces burdens on the patient.

In Step S3 of the first pulmonary embolism diagnosis support process shown in FIG. 2, the user may determine whether the blood flow is abnormal and identify the abnormal blood flow region, based on the blood flow information. For example, the controller 31 of the diagnosis console 3 displays the blood flow information (in the form of an image) on the display 34; and the user interprets the blood flow information and inputs the interpretation result on whether the pulmonary blood flow has a segmental defect (i.e., whether the blood flow is abnormal) by manipulating the operation receiver 33. When the blood flow is abnormal, the user further inputs the abnormal blood flow region with the operation receiver 33. The controller 31 obtains the result of determination on whether the blood flow is abnormal (including the abnormal blood flow region), which is input by the user via the operation receiver 33. In step S6, the controller 31 generates diagnosis support information regarding pulmonary embolism, based on (i) the result of determination by the user on whether the blood flow is abnormal and (ii) the result of determination on whether the background lungs is abnormal based on the background lungs information.

In Step S5 of the first pulmonary embolism diagnosis support process shown in FIG. 2, the user may determine whether the background lungs are abnormal and identify the abnormal background lungs region, based on the background lungs information. For example, the controller 31 of the diagnosis console 3 displays the background lungs information (in the form of an image) on the display 34; and the user interprets the background lungs information and inputs the interpretation result on whether the background lungs are abnormal by manipulating the operation receiver 33. When the background lungs are abnormal, the user further inputs the abnormal background lungs region by manipulating the operation receiver 33. The controller 31 obtains the result of determination on whether the background lungs are abnormal (including the abnormal background lungs region), which is input by the user via the operation receiver 33. In Step S6, the controller 31 generates diagnosis support information regarding pulmonary embolism, based on (i) the result of determination by the user on whether the background lungs are abnormal and (ii) the result of determination on whether the blood flow is abnormal based on the blood flow information.

Second Embodiment

Next, a second embodiment of the present invention is described.

The configuration of the imaging system in the second embodiment is the same as that of the imaging system 100 in the first embodiment. Therefore, FIG. 1 is used herein, and the description of components that are common to the first embodiment is omitted. Hereinafter, the configuration and processes specific to the second embodiment are described.

The controller 31 of the diagnosis console 3 receives, as the background lungs information, (i) an image(s) obtained by a modality that performs imaging different from dynamic imaging (hereinafter called "different modality image") and/ or (ii) information generated based on the different modality image. Herein, the examinee in dynamic imaging is the same as the examinee in the imaging other than dynamic imaging. In the second embodiment, reception of the background lungs information corresponds to generation of the background lungs information.

Examples of the different modality image include a plain X-ray image of the chest and a CT image of the chest. The diagnosis console 3 is connected to a modality that performs imaging other than dynamic imaging or to a picture archiving and communication system (PACS) that stores and manages medical images generated by the modality over the communication network NT. The diagnosis console 3 obtains (receives) the different modality image from the modality that performs imaging other than dynamic imaging or from the PACS. When the different modality image is a plain X-ray image of the chest, the modality can be the imaging device 1.

Examples of the information generated based on the different modality image include numerical values obtained by analyzing the different modality image (values useful for analyzing the state of the background lungs) and information on whether the background lungs are abnormal based on the different modality image. The diagnosis console 3 is connected to an analysis device that analyzes the different modality image and a data management device that stores and manages reports and so forth containing information on whether the background lungs are abnormal over the communication network NT. The diagnosis console 3 obtains (receives), from the analysis device and data management device, information that is generated based on the different modality image.

Next, operation in the second embodiment is described.

Figure 15:
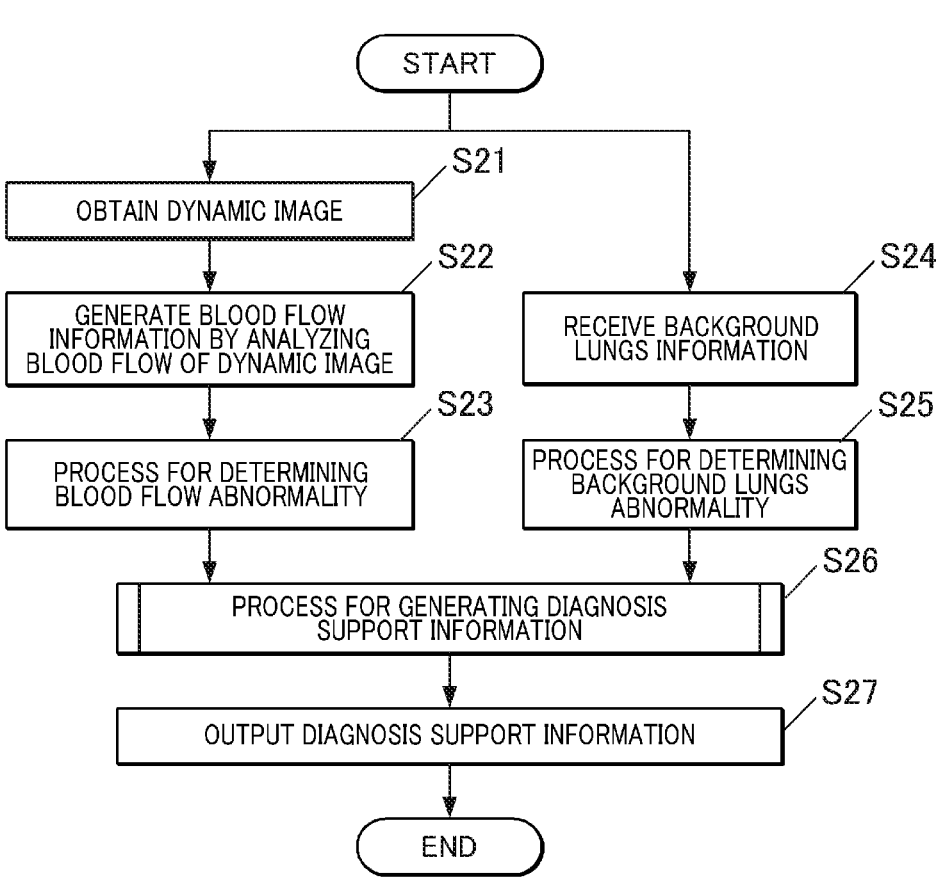
FIG. 15 is a flowchart of a second pulmonary embolism diagnosis support process in a second embodiment.

FIG. 15 is a flowchart showing the second pulmonary embolism diagnosis support process that is performed by the diagnosis console 3. The process is performed by the controller 31 in accordance with the program stored in the storage 32.

Steps S21 to S23 are the same as Steps S1 to S3 in the first pulmonary embolism diagnosis support process shown in FIG. 2, and the explanation thereof is omitted.

In the second pulmonary embolism diagnosis support process, a dynamic image is not used in the process regarding the background lungs. More specifically, Steps S24 and S25 are performed in parallel with Steps S21 to S23 or before/after Steps S21 to S23.

The controller 31 obtains, as the background lungs information, the different modality image of the examinee that is the same as the examinee of dynamic imaging and/or information generated based on the different modality image via the communication unit 35 (Step S24). For example, the controller 31 receives a plain X-ray image(s) of the chest or a CT image(s) of the chest from the modality that performs imaging other than dynamic imaging or the PACS, via the communication unit 35. As the background lungs information, the controller 31 may also receive (i) numerical values obtained by analyzing the different modality image or (ii) reports containing information on whether the background lungs are abnormal from external devices (e.g., the analysis device, data management device) via the communication unit 35.

Next, the controller 31 performs the process for determining background lungs abnormality (Step S25). More specifically, the controller 31 automatically determines whether there is an abnormality in the background lungs, based on the background lungs information. For example, the controller 31 analyzes the background lungs information (e.g., the plain X-ray image of the chest, the CT image of the chest) and, when detecting a shadow in the background lungs, the controller 31 determines that the background lungs are abnormal. When the background lungs information includes numerical values obtained by analyzing the different modality image, the controller 31 determines whether the background lungs are abnormal, based on the comparison of the numerical values with a predetermined threshold or a reference range. When the background lungs information includes information on whether the background lungs are abnormal, the controller 31 also obtains information on whether the background lungs are abnormal.

The controller 31 also identifies an abnormal region in the background lungs (abnormal background lungs region). The controller 31 stores the abnormal background lungs region in the storage 32.

After Step S23 and Step S25, the controller 31 performs the process for generating diagnosis support information (Step S26). The process for generating diagnosis support information is the same as the process described with reference to FIG. 14.

The controller 31 outputs diagnosis support information regarding the pulmonary embolism (Step S27). More specifically, the controller 31 displays diagnosis support information regarding pulmonary embolism on the display 34.

The second pulmonary embolism diagnosis support process ends.

As described above, in the second embodiment, the diagnosis support information regarding pulmonary embolism is generated based on (i) a dynamic image(s) and (ii) an image(s) obtained by a modality that performs imaging different from dynamic imaging (e.g., plain X-ray image of the chest, CT image of the chest). The second embodiment does not require administration of a contrast agent or radio-pharmaceutical to the patient, and is therefore low invasive. Further, the imaging device 1, which performs dynamic imaging, is less expensive and requires less preparation for examination than modalities that have been conventionally used for diagnosing pulmonary embolism. Thus, the first embodiment allows quick and low-cost diagnosis of pulmonary embolism that can be repeated and that reduces burdens on the patient.

Further, the background lungs information is (i) an image (s) which may have already been obtained in the previous examination (e.g., plain X-ray imaging, CT) or (ii) information generated based on such an image. Therefore, the patient does not have to undergo an examination merely for generating the background lungs information. This reduces burdens on the patient.

In Step S23 of the second pulmonary embolism diagnosis support process shown in FIG. 15, the user may determine whether the blood flow is abnormal and identify the abnormal blood flow region, based on the blood flow information. For example, the controller 31 of the diagnosis console 3 displays the blood flow information (in the form of an image) on the display 34; and the user interprets the blood flow information and inputs the interpretation result on whether the pulmonary blood flow has a segmental defect (i.e., whether the blood flow is abnormal) by manipulating the operation receiver 33. When the blood flow is abnormal, the user further inputs the abnormal blood flow region with the operation receiver 33. The controller 31 obtains the result of determination on whether the blood flow is abnormal (including the abnormal blood flow region), which is input by the user via the operation receiver 33. In Step S26, the controller 31 generates diagnosis support information regarding pulmonary embolism, based on (i) the result of determination by the user on whether the blood flow is abnormal and (ii) the result of determination on whether the background lungs are abnormal based on the background lungs information.

In Step S25 of the second pulmonary embolism diagnosis support process shown in FIG. 15, the user may determine whether the background lungs are abnormal and identify the abnormal background lungs region, based on the background lungs information. For example, the controller 31 of the diagnosis console 3 displays the background lungs information (in the form of an image) on the display 34; and the user interprets the background lungs information and inputs the interpretation result on whether the background lungs are abnormal by manipulating the operation receiver 33. When the background lungs are abnormal, the user further inputs the abnormal background lungs region by manipulating the operation receiver 33. The controller 31 obtains the result of determination on whether the background lungs are abnormal (including the abnormal background lungs region), which is input by the user via the operation receiver 33. In Step S26, the controller 31 generates diagnosis support information regarding pulmonary embolism, based on (i) the result of determination by the user on whether the background lungs are abnormal and (ii) the result of determination on whether the blood flow is abnormal, based on the blood flow information.

The embodiments described above are examples of the pulmonary embolism diagnosis support apparatus, the pulmonary embolism diagnosis support method, and the storage medium of the present invention. The embodiments are not intended to limit the present invention. The detailed configurations and operations of the components constituting the apparatuses can also be appropriately modified within the scope of the present invention.

For example, in the above embodiments, in the process for generating diagnosis support information (FIG. 14, Step S6 in FIG. 2, Step S26 in FIG. 15), the diagnosis support information regarding pulmonary embolism is generated based on the result of determination on (i) whether the blood flow is abnormal and (ii) whether the background lungs are abnormal. However, the diagnosis support information regarding pulmonary embolism may be generated based on the blood flow information and the background lungs information.

Further, the diagnosis support information regarding pulmonary embolism may be generated based on (i) the result of determination on whether the blood flow is abnormal and (ii) the background lungs information.

Further, the diagnosis support information regarding pulmonary embolism may be generated based on (ii) the blood flow information and (i) the result of determination on whether the background lungs are abnormal.

If the result of determination on whether the blood flow is abnormal is not obtained before the process for generating diagnosis support information, the determination on whether the blood flow is abnormal may be made based on the blood flow information in performing the process for generating diagnosis support information, and the result of determination may be used.

If the result of determination on whether the background lungs are abnormal is not obtained before the process for generating diagnosis support information, the determination on whether the background lungs are abnormal may be made based on the background lungs information in performing the process for generating diagnosis support information, and this result of determination may be used.

As an example of outputting the diagnosis support information regarding pulmonary embolism, the controller 31 of the diagnosis console 3 displays the support information regarding pulmonary embolism. Instead, the controller 31 may send the diagnosis support information regarding pulmonary embolism to an external device via the communication unit 35. The controller 31 of the diagnosis console 3 may also store the diagnosis support information regarding pulmonary embolism in a recording medium.

The operation instructions to the diagnosis console 3 and the processing result (e.g., diagnosis support information) may be made by manipulating an operation terminal provided outside the diagnosis console 3.

The diagnosis console 3 may be installed in or attached to the imaging console 2, and only the program function of the diagnosis console 3 may be performed by the controller 21 of the imaging console 2.

For another example, the function of the diagnosis console 3 may be provided to the PACS or a cloud server. In the case, only the storage 32 of the diagnosis console 3 may be included in the storage of the PACS, and the information to be used by the diagnosis console 3 may be retrieved from the PACS or the cloud server on demand.

The object of blood flow analysis may be limited to (i) a dynamic image taken while the patient is holding his/her breath, (ii) a dynamic image of a patient in the lying posture, or (iii) a dynamic image that is obtained with a frame rate within a predetermined range (e.g., 10 frames per second or greater), for example.

Further, the blood flow analysis may involve comparison of a dynamic image of a patient in the standing posture with a dynamic image of the patient in the lying posture in order to take the gravitational effect into account.

In the above description, a nonvolatile semiconductor memory and/or a hard disk are disclosed as examples of the computer readable medium that stores the programs of various processes. However, the computer readable medium is not limited to these examples. As the computer readable medium, a portable storage medium, such as a CD-ROM, can also be used. Further, a carrier wave can be used as a medium to provide data of the programs via a communication line.

The invention claimed is:

1. A pulmonary embolism diagnosis support apparatus comprising a hardware processor that:

obtains a dynamic image of a chest of an examinee captured through radiographic dynamic imaging;

analyzes blood flow in the dynamic image to generate blood flow information based on signal values of pixels of regions related to pulmonary blood flow in the dynamic image;

generates background lungs information regarding background lungs of the examinee based on the dynamic image or based on an image captured by a modality different from dynamic imaging;

wherein the blood flow information includes information for determining whether an abnormality exists in the blood flow, and the background lungs information includes information for determining whether an abnormality other than the blood flow exists in the background lungs;

automatically generates diagnosis support information regarding pulmonary embolism, based on the blood flow information and the background lungs information; and outputs the diagnosis support information regarding pulmonary embolism.

2. The pulmonary embolism diagnosis support apparatus according to claim 1, wherein the hardware processor automatically determines whether the blood flow is abnormal, based on the blood flow information, and based on the background lungs information and the determination on whether the blood flow is abnormal, the hardware processor automatically generates the diagnosis support information regarding pulmonary embolism.

3. The pulmonary embolism diagnosis support apparatus according to claim 1, wherein the hardware processor automatically determines whether the background lungs are abnormal, based on the background lungs information, and based on the blood flow information and the determination on whether the background lungs are abnormal, the hardware processor automatically generates the diagnosis support information regarding pulmonary embolism.

4. The pulmonary embolism diagnosis support apparatus according to claim 1, wherein the hardware processor automatically determines whether the blood flow is abnormal, based on the blood flow information, the hardware processor automatically determines whether the background lungs are abnormal, based on the background lungs information, and based on the determination on whether the blood flow is abnormal and the determination on whether the background lungs are abnormal, the hardware processor automatically generates the diagnosis support information regarding pulmonary embolism.

5. The pulmonary embolism diagnosis support apparatus according to claim 1, wherein when the blood flow is abnormal but the background lungs are normal, the hardware processor generates the diagnosis support information that indicates a possibility of pulmonary embolism.

6. The pulmonary embolism diagnosis support apparatus according to claim 1, wherein when (i) the blood flow is abnormal and (ii) a region of the background lungs corresponding to a region of the abnormal blood flow is abnormal, the hardware processor generates the diagnosis support information that indicates a possibility of a disease different from pulmonary embolism.

7. The pulmonary embolism diagnosis support apparatus according to claim 1, wherein when the blood flow is normal, the hardware processor generates the diagnosis support information that indicates no possibility of pulmonary embolism.

8. The pulmonary embolism diagnosis support apparatus according to claim 1, wherein the hardware processor generates the background lungs information, based on one or more frame images included in the dynamic image.

9. The pulmonary embolism diagnosis support apparatus according to claim 1, wherein as the background lungs information, the hardware processor receives (i) an image captured by a modality that performs imaging different from dynamic imaging or (ii) information generated based on the image captured by the modality.

10. The pulmonary embolism diagnosis support apparatus according to claim 1, wherein the hardware processor obtains the background lungs information regarding background lungs of the examinee based on a plain X-ray image captured by a modality different from dynamic imaging.

11. The pulmonary embolism diagnosis support apparatus according to claim 1, wherein wherein the diagnosis support information indicates a possibility of pulmonary embolism when the blood flow information indicates that the blood flow is abnormal and the background lungs information indicates that the background lungs are normal, the diagnosis support information indicates a possibility of a disease different from pulmonary embolism when the blood flow information indicates that the blood flow is abnormal and the background lungs information indicates that a region of the background lungs corresponding to a region of the abnormal blood flow is abnormal, and the diagnosis support information indicates no possibility of pulmonary embolism when the blood flow information indicates that the blood flow is normal.

12. The pulmonary embolism diagnosis support apparatus according to claim 1, wherein wherein the hardware processor determines the blood flow is abnormal based on a decrease of blood flow in a region or based on a comparison of values of the blood flow with a predetermined threshold or predetermined range, and wherein the hardware processor determines the background lungs are abnormal based on a finding of a morphological abnormality or based on a comparison of a change amount of a specific component of the background lungs with a predetermined threshold or predetermined range.

13. A pulmonary embolism diagnosis support method comprising:

obtaining a dynamic image of a chest of an examinee captured through radiographic dynamic imaging;

analyzing blood flow in the dynamic image to generate blood flow information based on signal values of pixels of regions related to pulmonary blood flow in the dynamic image;

generating background lungs information regarding background lungs of the examinee based on the dynamic image or based on an image captured by a modality different from dynamic imaging;

wherein the blood flow information includes information for determining whether an abnormality exists in the blood flow, and the background lungs information includes information for determining whether an abnormality other than the blood flow exists in the background lungs;

automatically generating diagnosis support information regarding pulmonary embolism, based on the blood flow information and the background lungs information; and outputting the diagnosis support information regarding pulmonary embolism.

14. A nontransitory computer-readable storage medium storing a program that causes a compute to:

obtain a dynamic image of a chest of an examinee captured through radiographic dynamic imaging;

analyzing blood flow in the dynamic image to generate blood flow information based on signal values of pixels of regions related to pulmonary blood flow in the dynamic image;

generate background lungs information regarding background lungs of the examinee based on the dynamic image or based on an image captured by a modality different from dynamic imaging;

wherein the blood flow information includes information for determining whether an abnormality exists in the blood flow, and the background lungs information includes information for determining whether an abnormality other than the blood flow exists in the background lungs;

automatically generate diagnosis support information regarding pulmonary embolism, based on the blood flow information and the background lungs information; and output the diagnosis support information regarding pulmonary embolism.

* * * * *